United States Patent [19]

Sachse

[11] Patent Number: 5,409,468

[45] Date of Patent: Apr. 25, 1995

[54] ARRANGEMENT COMPRISING A URETER TUBE, AN AUXILIARY TUBE AS WELL AS A MANDRIN

[76] Inventor: Hans Sachse, Lerchenstrasse 55, 8500 Nürnberg, Germany

[21] Appl. No.: 942,883

[22] Filed: Sep. 11, 1992

[30] Foreign Application Priority Data

Sep. 13, 1991 [DE] Germany .......... 41 30 433.0
Dec. 13, 1991 [DE] Germany .......... 41 41 155.2

[51] Int. Cl.⁶ .................................. A61M 25/00
[52] U.S. Cl. .................................. 604/282; 604/280; 128/657
[58] Field of Search ............... 604/170, 282, 281, 280, 604/166, 264, 8–10, 93, 246, 249, 164, 256; 128/656–658, 772

[56] References Cited

U.S. PATENT DOCUMENTS

| 4,212,304 | 7/1980 | Finney | 604/170 |
| 4,787,884 | 11/1988 | Goldberg | 604/8 |
| 4,871,356 | 10/1989 | Haindl et al. | 604/247 |
| 4,874,360 | 10/1989 | Goldberg et al. | 604/8 |
| 4,931,037 | 6/1990 | Wetterman | 604/8 |
| 4,957,479 | 9/1990 | Roemer | 604/8 |
| 5,116,309 | 5/1992 | Coll | 604/8 |

FOREIGN PATENT DOCUMENTS

| 3824244 | 1/1990 | Germany . |
| 3922126 | 1/1990 | Germany . |
| 3900738 | 7/1990 | Germany . |
| 9015815 U | 4/1991 | Germany . |

Primary Examiner—C. Fred Rosenbaum
Assistant Examiner—V. Alexander
Attorney, Agent, or Firm—Keil & Weinkauf

[57] ABSTRACT

A catheter device having a ureter tube, an auxiliary tube, and a moveable mandrin. The upper tip of the ureter tube has an inherent curvature. The upper tip of the mandrin has an inherent curvature. The upper tip of the mandrin can project above the upper tip of the ureter tube. A hollow space inside the mandrin contains a steering wire.

18 Claims, 4 Drawing Sheets

ARRANGEMENT COMPRISING A URETER TUBE, AN AUXILIARY TUBE AS WELL AS A MANDRIN

The starting point of the present invention starts is represented by an arrangement according to the preamble of claim 1. Such an arrangement is described in U.S. Pat. No. 4,212,304. With such an arrangement it is possible to insert the ureter tube into the ureter. After removal of the solid mandrin, the arrangement is held in the ureter by its flexible inherent curvature in the form of a hook ("pig-tail") at both ends at the renal pelvis and at the inner wall of the bladder. In this connection, U.S. Pat. No. 3,890,977 describes an alloy having a so-called "memory" effect. A catheter is shaped at a high temperature in order to guarantee its anchoring in an organ of a body. Thereafter the catheter is given a shape at a temperature below its transition temperature which shape facilitates the insertion of the catheter. After positioning of the catheter in the organ of the body, the catheter is given again the shape by heating above its transition temperature which shape gives an anchorage in the organ of the body. Such a method is complicated and does in no way make obvious the invention described hereinafter.

The same applies for the object of the German Patent Application DE-OS 3,921,634 which relates to a urethra catheter having a main body being soft and flexible and a proximal hook section. Said hook section is stiffer in order to avoid a migration of the urethra catheter from the renal pelvis.

In practice, however, there are from time to time cases where the physician has difficulty pushing the ureter tube, which has a certain thickness, through the ureter and into the renal pelvis because of the extremely narrow passages and/or courses of the ureter having bends or corners. In connection therewith, there is the problem of introducing a contrast medium into the ureter in order to show the physician, during the placement of the ureter tube, the course of the ureter and the position of the ureter tube in its respective stage. In the prior art, as described in U.S. Pat. No. 4,212,304, an introduction of an X-ray contrast medium into the ureter was not possible. In a complicated way, the necessary X-ray contrast medium had to be introduced into the ureter by separate measures before the ureter tube could be inserted. This extra step is time-wasting for the physician and unpleasant for the patient because an equipment has to be introduced twice.

SUMMARY OF THE INVENTION

An object of this invention is to change the mentioned simple arrangement described in U.S. Pat. No. 4,212,304, in order to enable an easy insertion of the ureter tube, especially in cases where the ureter has narrowed passages and/or has a course full of corners. The object can be achieved with an arrangement for the insertion of a ureter tube into the ureter or renal pelvis, which arrangement comprises a ureter tube (A), an auxiliary tube (B) and a mandrin (C), wherein at least the upper tip of the ureter tube (A) has an inherent curvature, wherein the mandrin (C) at its upper end has an inherent curvature, the mandrin (C) has in the hollow-space inside of the mandrin (C) a steering wire (18) being essentially stiff against bending and movable in the longitudinal direction of the mandrin (C), and the upper tip (12) of the ureter tube (A) allows the mandrin to project above the tip of the ureter tube (A) at least with its section of its inherent curvature.

The mandrin (C) can be a single mandrin or a double mandrin consisting of an outer mandrin (5) and an inner mandrin (4), movable in and in the longitudinal direction relative to the outer mandrin and wherein ureter tube (A) and auxiliary tube (B) are slidable over the double mandrin. If the mandrin (C) is a double mandrin, the inner mandrin (4) is hollow and the steering wire (18) is in the hollow-space of the inner mandrin (4) from which it can be pulled out, and the inner mandrin (4) has an inherent curvature (4d) and the inner mandrin (4) projects from the tip (12) of the ureter tube facing toward the patient. In a preferred embodiment of the invention the upper tip (4d) of the inner mandrin (4) is closed against a passage of X-ray contrast medium and/or the steering wire. In addition to the advantages of an inherent curvature of the tip of the ureter tube, the present invention gives the additional advantages of an inherent curvature of the tip of the mandrin, i.e. of the upper section of the mandrin facing the patient. The term tip of the ureter tube shall mean the proximal or upper end of the ureter tube which is inserted into the ureter. The term tip of the mandrin (respectively tip of the inner mandrin) shall mean the proximal or end facing the patient. The term inherent curvature is known in the art to be a curved shape given to the tip section of the ureter tube which shape can for the insertion of the ureter tube be straightened by means of the mandrin. After reaching the final position, where the upper tip of the ureter tube is in the renal pelvis and the lower end is in the bladder, the mandrin is pulled out. Thereby the ends of the ureter tube take again the shape of the inherent curvature by which, without migration, they are held at the inner wall of the bladder and in the renal pelvis. It is also possible to have a similar inherent curvature of the tip section of the mandrin which clearly projects from the tip of the ureter tube. A steering wire in the mandrin can compensate the inherent curvature and effect a straightening of the tip of the mandrin. The tip of the mandrin can have a variable curvature and can be pushed out of the tip of the ureter tube to a large extent. Thus, it can, more easily than the thicker tip of the ureter tube, prepare a way to the renal pelvis in cases where the ureter has extreme narrow passages and/or the course of the ureter is full of corners. The thicker ureter tube can then follow such prepared way.

In a preferred embodiment of an arrangement according to this invention, the inherent curvature of the tip (12) of the ureter tube and the inherent curvature of the upper section (4c) of the mandrin have and keep the same direction of curvature. Such fixation of the same direction of the curvatures can be achieved by cross-section shapes of the curvatures fitting together. The characteristic of such structure is to prevent that the strengths of both inherent curvatures partly or wholly compensate each other.

In the arrangement according to this invention the mandrin can be a single mandrin having the shape of a hollow tube having a steering wire inside of the mandrin. Alternatively the mandrin is preferably a hollow double mandrin. The double mandrin consists of an outer mandrin and an inner mandrin. The inner mandrin has in its upper tip section the inherent curvature and contains inside of it the steering wire.

The upper tip of the inner mandrin can be closed against a passage of X-ray contrast medium and of the steering wire or have at least one upper opening for the X-ray contrast medium as described in more detail below.

In a preferred arrangement according to this invention there is a releasable clamping or bolting between the mandrin (inner mandrin 4 or single mandrin 21) and its steering wire (18) which can be releasably clamped or bolted, i.e. released, from the outside.

A releasable clamping or bolting mechanism enables it to push jointly the mandrin and the steering wire to the ureter tube and, in particular, to such a position where by at least the section of the mandrin having the inherent curvature projects from the tip of the ureter tube. After release of the clamping or bolting, the curved section of the mandrin can be straightened or brought to its hook shape again by a respective move of the steering wire.

Moreover, the present invention provides a solution to the mentioned problem with respect to the introduction of an X-ray contrast medium into the ureter and from there to the renal pelvis. In the arrangement according to this invention the steering wire can be pulled out from the mandrin (either a single mandrin, or the inner mandrin in a double mandrin embodiment) and the thereby formed opening toward the lower end (toward the physician) can be closed. In a preferred embodiment of the arrangement according to this invention the single mandrin or inner mandrin is hollow, the hollow space inside of the single mandrin or inner mandrin in the section of the upper tip has at least one outlet opening for the passage of an X-ray contrast medium, the outlet opening has an entry to the ureter via a preferably front-side opening of the tip of the ureter tube, and the hollow space inside of the mandrin (single mandrin or inner mandrin) has at the other end, projecting from the auxiliary tube, a connecting piece or opening for the introduction of the X-ray contrast medium. The mandrin (single mandrin or inner mandrin) can have in its walls at least one lateral upper outlet opening which is preferably directly below the section of the inherent curvature of the tip of the mandrin (single mandrin or inner mandrin) or positioned a greater distance below the tip of such mandrin and opposite the drainage opening of the ureter tube.

In an arrangement according to this invention the single mandrin or inner mandrin or outer mandrin can have a connecting piece for the introduction of the X-ray contrast medium or an attachment for affixing a syringe containing the X-ray contrast medium. Such arrangements provide a faster and simpler introduction of the X-ray contrast medium is made possible, requiring fewer manipulations by the physician. Even if the inner hollow space of the single mandrin or inner mandrin is partially occupied by the steering wire there still remains a lumen or a ring-cylindrical hollow space, respectively, between the steering wire and the inner wall of the single mandrin or of the inner mandrin for the passage of an X-ray contrast medium. Thus, the physician can, during the shoving in of ureter tube, auxiliary tube and the mandrin, stiffening the ureter tube, steadily inject X-ray contrast medium and thus control by radiograph the position of the ureter tube and its tip. Repeated injections of the X-ray contrast medium during the examination are possible. This results in great advantages for the patient and the physician. If the steering wire is pulled out from the mandrin the cross-section of the passage for the X-ray contrast medium is enlarged.

Further, the invention starts from an arrangement as described in the German Utility Model 9,015,815, but the mandrin disclosed has no inherent curvature. Another embodiment of the present invention gives a further possible combination of an arrangement of a mandrin having an inherent curvature in its upper section with a steering wire the use of a double mandrin. The use of a double mandrin is sometimes advantageous and allows, to a certain extent, the injection of an X-ray contrast medium into the ureter even when the steering wire has not been pulled out.

Another preferred arrangement according to this invention comprises a hollow ureter tube, a double mandrin with an outer mandrin and an inner mandrin, movable in the longitudinal direction relative to the outer mandrin, and an auxiliary tube, wherein ureter tube and auxiliary tube are slidable over the double mandrin and wherein the upper tip of the ureter tube, being opposite to the auxiliary tube, has at its front side a central opening, there are the outer mandrin and the ureter tube in the insertion position releasably connected, e.g. by a clamping by means of a thickening (increased diameter) of the outer mandrin or by means of an insertion between outer mandrin and ureter tube in such a way that the clamping and friction between outer mandrin and ureter tube can be released by pulling the outer mandrin in longitudinal direction or by a releasable screwing together of the outer mandrin and the ureter tube. It is preferred that in the insertion position, the ureter tube and outer mandrin are releasably but firmly connected. They can be clamped together in the end section of the auxiliary tube. The term "insertion configuration" shall mean the configuration of ureter tube, mandrin (in particular double mandrin) and auxiliary tube that they have relative to each other during the insertion of the whole configuration into the ureter and also during the introduction of the X-ray contrast medium into the ureter. The steering wire can be simultaneously clamped too. Such releasable connection between the outer mandrin and ureter tube is described in German Patent Application DE-OS 3,900,738 filed by the Applicant. After use of a clamping connection at the end section of the auxiliary tube, the ureter tube, the mandrin or double mandrin and the auxiliary tube form a functional unit. For facilitating the insertion, the functional unit allows forward, backward and rotational movements of the ureter tube and of the curvatures of the tip of the ureter tube, and allows after proper positioning of the ureter tube for the easy removal of the mandrin and auxiliary tube. The clamping or friction between outer mandrin and ureter tube can be released by pulling the outer mandrin in a longitudinal direction while at the same time the auxiliary tube avoids a movement of the ureter tube. The mentioned friction can be increased by roughening the surfaces or by providing them with grooves. A releasable connection between outer mandrin and ureter tube is also possible by the use of a releasable screwing as described in the German Patent Application DE-OS 3,824,244. The releasable screwing also allows the creation of a functional unit of the two parts and allows said rotational, forward and backward movements of the arrangement.

Another preferred embodiment of the arrangement according to this invention comprises a hollow ureter tube, a double mandrin with an outer mandrin and an inner mandrin movable in the longitudinal direction relative to the outer mandrin, and an auxiliary tube, wherein ureter tube and auxiliary tube are slidable over the double mandrin, wherein the upper tip of the ureter tube, being opposite to the auxiliary tube, has at its front side a central opening, and wherein preferably the outer mandrin and the ureter tube in the insertion position are releasably connected, as described above, the hollow inner mandrin has in the section of its upper tip at least one upper outlet opening from the hollow space inside of the inner mandrin for the passage of an X-ray contrast medium and the outlet opening has an entry to the ureter via a preferably front side opening of the tip of the ureter tube, and the hollow space inside of the inner mandrin has at the other end of the inner mandrin, projecting from the auxiliary tube, a connecting piece or opening for the introduction of the X-ray contrast medium into the hollow space inside of the inner mandrin. In such arrangement the hollow space enclosed by the inner mandrin gives a passage for the X-ray contrast medium from the inlet opening outside of the body until into the ureter. For the transport of the X-ray contrast medium into the ureter, the inner mandrin does not have to be pulled out from the ureter tube, but can remain in its insertion configuration. This saves time for the surgeon. In the preferred embodiment of the arrangement, the arrangement of ureter tube, double mandrin and auxiliary tube can be moved simultaneously with the introduction of the X-ray contrast medium, and, if necessary, the upper section of the inner mandrin, having the inherent curvature, can be pushed out of the tip of the ureter tube and used as a "path-finder" or guide for the tip of the ureter tube until the tip of the ureter tube has reached its final position in the renal pelvis. Also the inner mandrin alone can be moved relative to the ureter tube. When moving back the inner mandrin, the inherent curvature of the tip of the ureter tube will be no longer straightened, thus the tip of the ureter tube will form again its curved shape and adapt to a curved course of the ureter. The last-mentioned advantages are very important for the physician as it allows him to simultaneously move the ureter tube and to radiographically examine ureter and renal pelvis.

Further advantages and embodiments of the present invention can be seen in or easily derived from the claims, from the description given herein and from the drawings relating thereto.

DESCRIPTION OF THE PREFERRED EMBODIMENT

Figure 1:
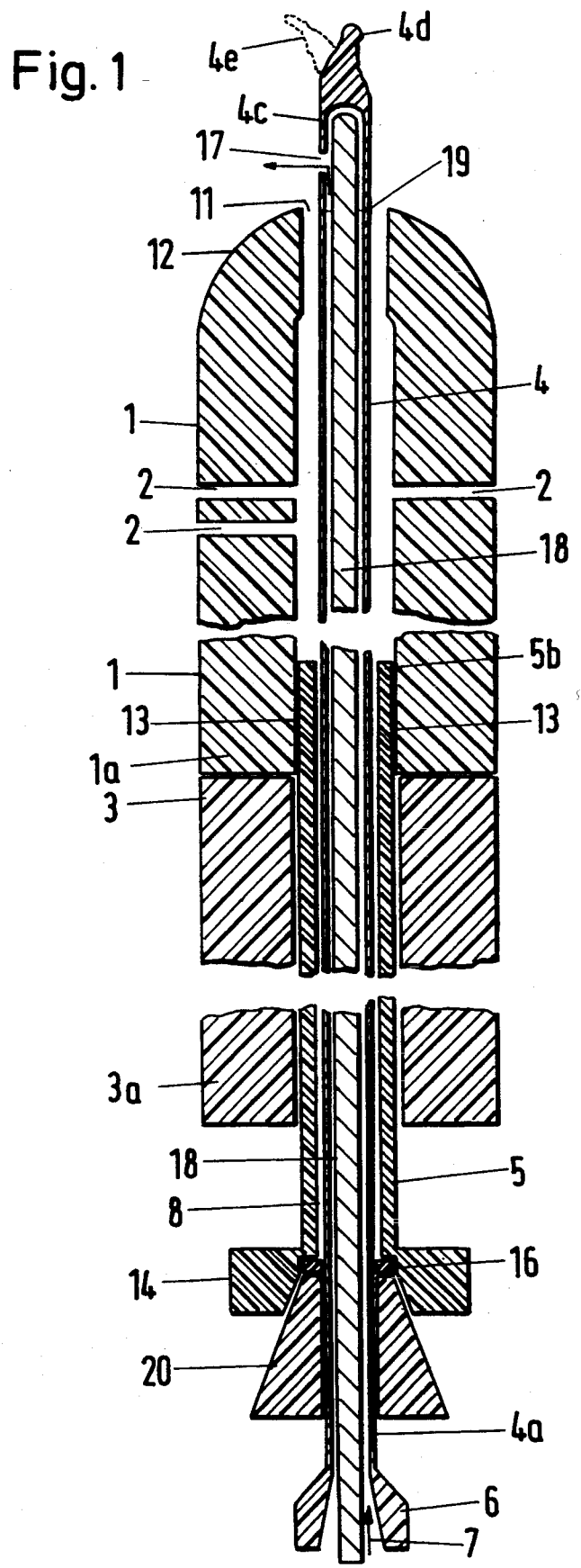
FIG. 1 shows a first embodiment of the invention in longitudinal section.

FIG. 1 shows a first embodiment of the invention comprising a ureter tube (1) being opened at both sides, drainage channels (2) and at its upper tip (12) an outlet opening (11). The ureter tube (1) is hollow and contains inside a hollow-cylindrical double mandrin (4;5). The double mandrin consists of an inner mandrin (4) and an outer mandrin (5). As shown the tip (4d) and the section (4c) of the inner mandrin projects from the tip (12) of the ureter tube facing toward the patient. Section (4c) has an inherent curvature indicated by a dotted-line. The inherent curvature is in the section from the tip (4d) to about the line (19). This section has at least one lateral outlet opening (17) for the passage of an X-ray contrast medium. Such medium is injected in the part of arrangement facing toward the physician as indicated by arrow (7) and reaches the ureter via the cylindrical hollow space between the inner mandrin (4) and steering wire (18) and via the openings (17). Furthermore, there is an auxiliary tube (3) contacting, with its upper end, the lower end (1a) of the ureter tube, and can be releasably clamped together with the outer mandrin (5), inner mandrin (4) and steering wire (18) in its lower part (not shown).

The upper section (5b) of the outer mandrin is connected with the lower section (1a) of the ureter tube by means of clamping (13). Such clamping can be released by pulling down the outer mandrin, by means of a handle (14). After having finished the insertion of the ureter tube into the ureter, the outer mandrin can be removed by pulling it down at the handle (14), overcoming the clamping force between the parts (1a),(13), and (15). The auxiliary tube (3) prevents the ureter tube (1) from being pulled down too. After having pulled out the outer mandrin, the auxiliary tube (3) can be withdrawn from the bladder and urethra. Such a procedure is known per se. Even when the outer mandrin and the ureter tube are clamped together, the inner mandrin (4) can always be pushed upwards, or in the direction opposite to the direction of the arrow (7) pulled out, if necessary. For the insertion of the arrangement, auxiliary tube (3), outer mandrin (5) and inner mandrin (4) are clamped together by means of a releasable bolting or clamping . device, e.g., a clamping tape or clamping screw, preferably at the lower part (3a) of the auxiliary tube. By such clamping, one can reach the position of the insertion configuration which is described below. The inner mandrin (4) can, at its lower part (4a), be clamped together with the steering wire (18) (not shown). A syringe for the introduction of the X-ray contrast medium can be affixed at an attachment (6) of the lower part of the inner mandrin (4). A gasket (16) can be clamped by part (20) in order to avoid there a leakage of the X-ray contrasting medium. Outer mandrin (5) and inner mandrin (4) are elongated hollow cylinders. The inner mandrin is preferably made from an elastic metal or plastic tube.

The drainage channels (2) can be used to have an outlet of the X-ray contrast medium there, either in addition or alternatively to the outlet via the outlet openings (17).

The upper tip (4d) of the upper section (4c) of the inner mandrin is preferably closed and does not permit the efflux of the X-ray contrast medium or a projection of the upper end of the steering wire (18). The inherent curvature (4e) of section (4c) of the inner mandrin is provided by the manufacturer. In order to have such curvature be formed, the inner mandrin (4) or the mandrin (21) and the steering wire (18) are connected by a releasable clamping device as indicated e.g. in FIG. 2 by number (20).

Thus the treating physician is provided with an arrangement consisting of a thin inner mandrin and a thicker ureter tube where the tips of both have an inherent curvature. Depending on the shape and course of the ureter, the physician can, having regarded the X-ray photograph, decide if he stiffens and straightens the tip of the inner mandrin, or uses said tip in its curved pigtail shape for finding the way, or if he pulls back the inner mandrin into the ureter tube and finds the way to the renal pelvis by use of the ureter tube only. The pig-tail curvatures of both inherent curvatures, i.e., of the tips of the inner mandrin and of the ureter tube, go preferably into the same direction of what can be reached i.e. by oval cross-section shapes.

If not needed, it is recommended that the steering wire (18) be removed before the injection of the X-ray contrast medium according to arrow 7.

Figure 2:
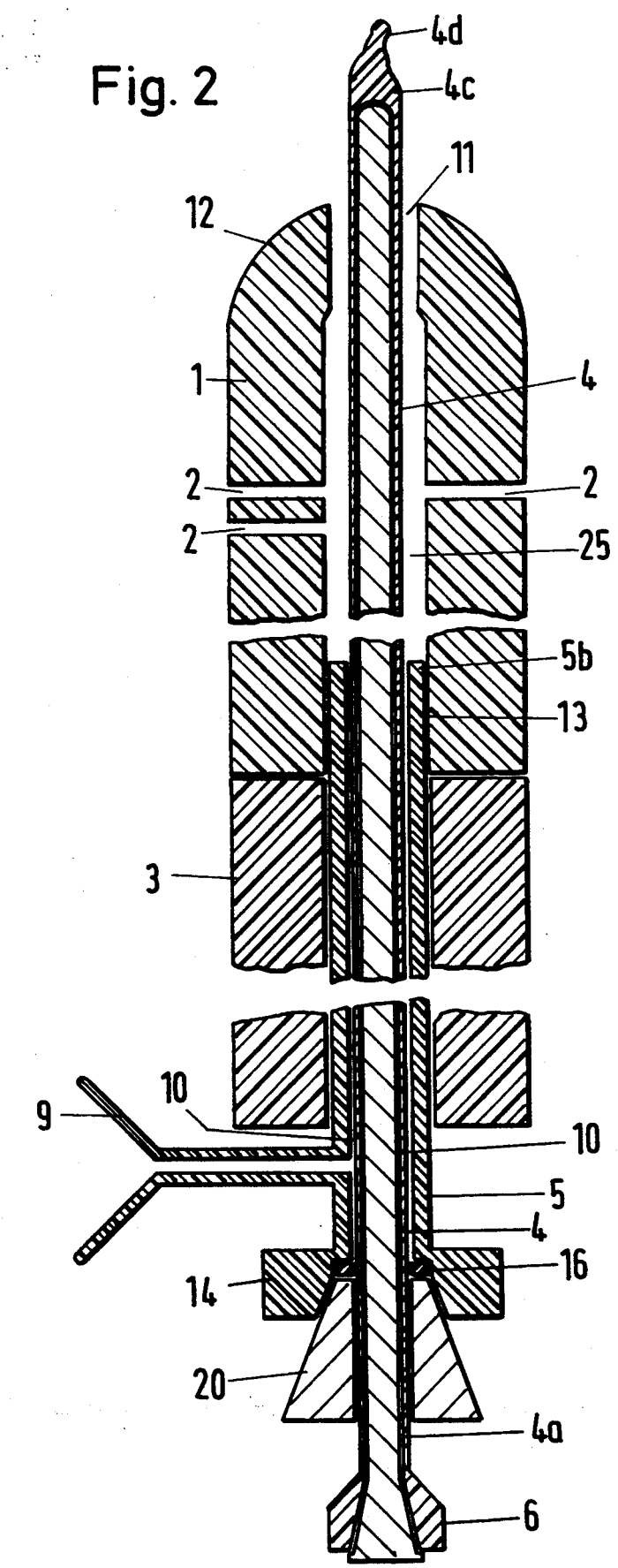
FIG. 2 shows a second embodiment of the invention in longitudinal section.

The embodiment of the invention according to FIG. 2 is analogous to the embodiment shown in FIG. 1. Therefore similar parts have the same numbers as used for the respective parts in FIG. 1. In the embodiment according to FIG. 2 the introduction of the X-ray contrast medium takes place via an attachment (9) to the cylindrical hollow space (10) between outer mandrin (5) and inner mandrin (4). After having reached the upper end (5b) of the outer mandrin the hollow space (10) is followed by a cylindrical hollow space (25) of the ureter tube around the inner mandrin which leads the X-ray contrast medium through the opening (11) of the tip (12) of the ureter tube into the ureter.

Figure 3:
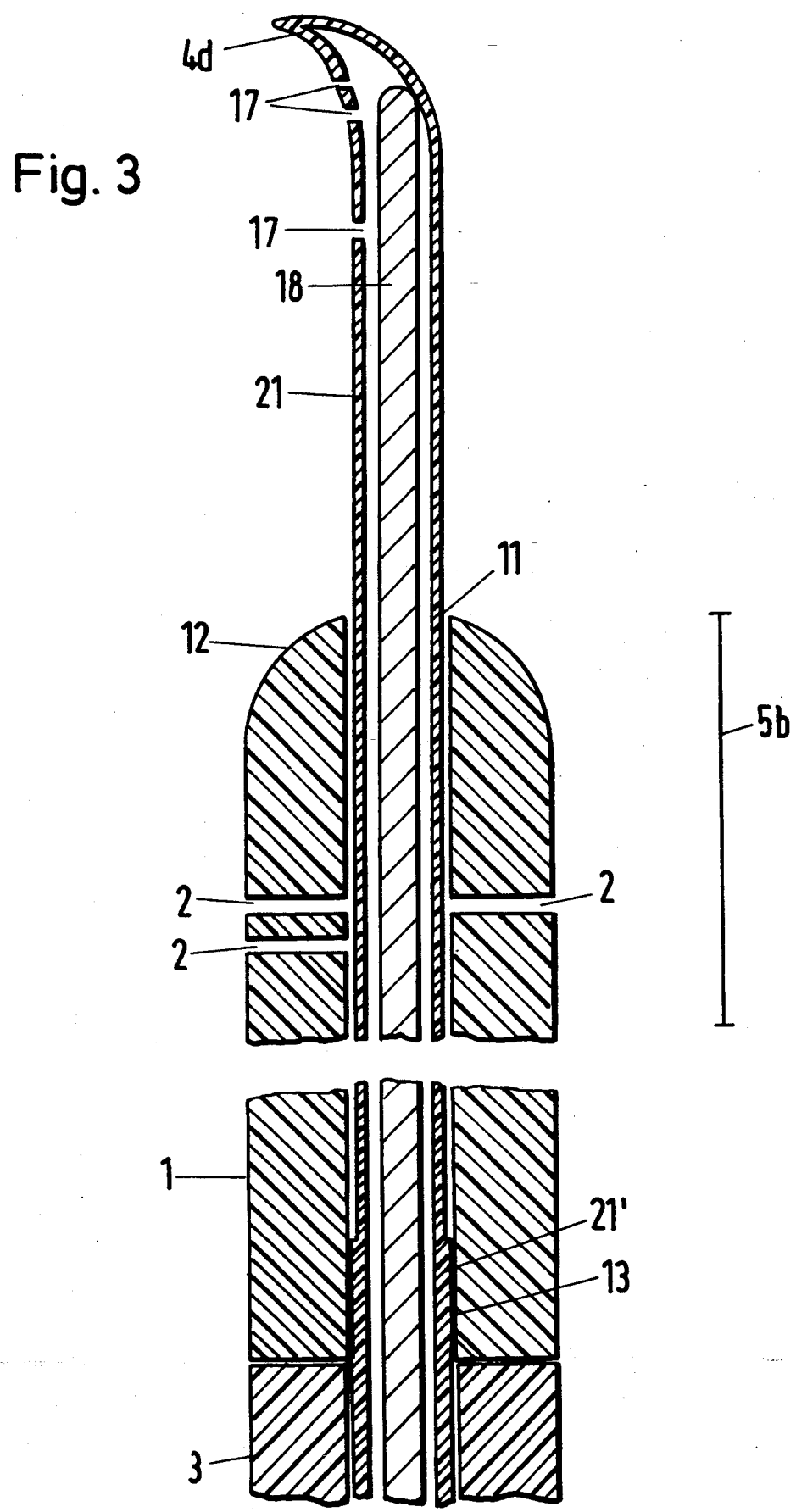
FIGS. 3 and 4 show the upper and lower part of a third embodiment of the invention in longitudinal section.
Figure 4:
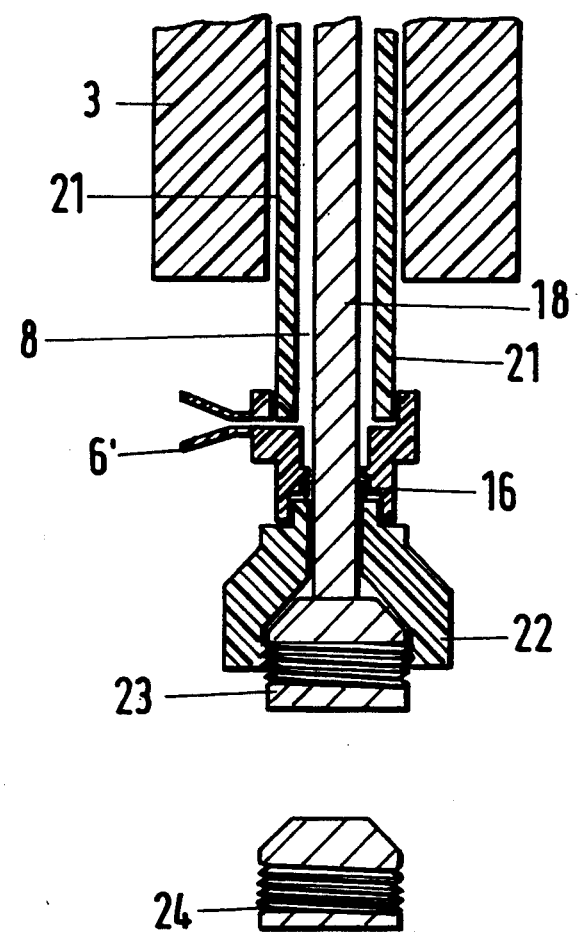

The third embodiment of this invention, according to FIGS. 3 and 4, shows that only one hollow mandrin (21) can enable the formation of the second inherent curvature and the passage of the X-ray contrast medium through the ureter tube into the ureter. A comparison of FIGS. 3 and 4 with FIG. 1 shows that the upper section of the mandrin having the inherent curvature can project to a variable extent above the tip (12) of the ureter tube. There is a small space between the inner wall of the ureter tube (1) and the outer wall of the mandrin (21). However, the space between mandrin (21) and the steering wire (18) is larger and makes it possible, as described below, that the X-ray contrast medium can be passed through coming from the connecting-piece 6' and entering the ureter via the opening (17). Otherwise the upper section of the mandrin has outlet openings (17) and also an inherent curvature (as explained above for the embodiments shown in FIGS. 1 and 2) and includes a steering wire (18). The same numbers used in FIGS. 1 and 2 are used here for the outlet openings of the ureter tube and other corresponding parts of the arrangement. Close to the lower part of the auxiliary tube (3) the mandrin (21) has a thickening (21'), which increases the diameter and can be clamped with the inner wall of the ureter tube (1) as indicated by number (13). The steering wire (18) can be screwed or bolted at its end section in different positions what is necessary if—departing from the drawings—the mandrin should have an open tip (4d). The X-ray contrast medium can be passed from the connecting-piece 6' through the cylindrical hollow space (8), existing between the inner wall of the mandrin and the steering wire (18), and via the openings (17) to the ureter. The auxiliary tube (3) is loosely shoved onto the outer wall of the thickening (21'). The connecting-piece 6' serves for affixing a syringe for the injection of the X-ray contrast medium. Apart from the auxiliary tube (3) the steering wire (18) and the mandrin (21) are releasably connected. A handle (22) has been screwed to the lower part (23) of the steering wire (18). After unscrewing, the steering wire (18) can be pulled out from the mandrin (if necessary) what facilitates the introduction of the X-ray contrast medium into the ureter after the closing screw (24) has been screwed on the handle (22) in order to avoid an efflux of the X-ray contact medium. However, the introduction of he X-ray contrast medium is possible too via the mentioned ring-cylindric hollow space or lumen (8) when the steering wire (18) has not been pulled out.

Features described for one of the embodiments of the invention can be used also in connection with other embodiments of the invention to the extent technically feasible.

I claim:

1. An arrangement having upper and lower ends for the insertion of a ureter tube into the ureter or renal pelvis, comprising a ureter tube, an auxiliary tube and a mandrin, each having an upper and a lower end, said mandrin being movable in longitudinal direction relative to the ureter tube, and the auxiliary tube and the ureter tube are slidable over the mandrin, and at least the upper tip of the ureter tube has an inherent curvature, wherein the mandrin in its upper end has an inherent curvature, the mandrin has a hollow space inside of the mandrin, said hollow space housing a steering wire being essentially stiff against bending and movable in the longitudinal direction of the mandrin, and the upper tip of the ureter tube allows the mandrin to project above the tip of the ureter tube at least with the section of the inherent curvature of the mandrin.

2. An arrangement according to claim 1, wherein the mandrin is a double mandrin containing an outer mandrin and an inner mandrin and the upper tip of the inner mandrin is closed against a passage of x-ray contrast medium and of the steering wire.

3. An arrangement according to claim 1 wherein
the inherent curvature of the tip of the ureter tube and the inherent curvature of the upper section of the mandrin have and keep the same direction of curvature.

4. An arrangement according to claim 1, wherein
the mandrin is a single mandrin having the shape of a hollow tube.

5. An arrangement according to claim 1 wherein
the mandrin is a double mandrin consisting of an outer mandrin and an inner mandrin.

6. An arrangement according to claim 5 wherein the inner mandrin, being movable in the longitudinal direction relative to the outer mandrin, has in its upper end said inherent curvature of the mandrin and the hollow inner mandrin contains said movable steering wire.

7. An arrangement according to claim 6 wherein the outer mandrin and the ureter tube in the insertion position are releasably connected and wherein the upper tip of the ureter tube has at its front-side a central opening.

8. An arrangement according to claim 7 wherein the outer mandrin and the ureter tube are releasably connected by a clamping in such a way that the friction between outer mandrin and ureter tube can be released by pulling the outer mandrin the longitudinal direction.

9. An arrangement according to claim 6 wherein the hollow inner mandrin has it its upper section at least one outlet opening for the passage of the X-ray contrast medium from the hollow space inside of the inner mandrin to the ureter via a front-side opening of the tip of the ureter tube and the hollow inner mandrin has at its lower end, projecting from the auxiliary tube, a connecting-piece or opening for the introduction of the X-ray contrast medium into the hollow space inside of the inner mandrin.

10. An arrangement according to claim 1 having a releasable clamping or bolting between the mandrin and its steering wire which releasable clamping can be operated from outside.

11. An arrangement according to claim 1, wherein the steering wire can be pulled out from the mandrin to form an opening toward the lower end, which opening can be closed.

12. An arrangement according to claim 1,
wherein the mandrin is hollow,
wherein the hollow-space inside of the mandrin in the section of its upper tip has at least one upper outlet opening for the passage of an X-ray contrast medium and the outlet opening has an entry to the ureter via a front-side opening of the tip of the ureter tube, and
wherein the hollow space inside of the mandrin at the lower end, projecting from the auxiliary tube has a connecting-piece or opening for the introduction of the X-ray contrast medium.

13. An arrangement according to claim 1, having between the steering wire and the inner wall of the mandrin or of the inner mandrin a ring-cylindrical hollow-space for the passage of the X-ray contrast medium.

14. An arrangement according to claim 1 wherein the mandrin or inner mandrin has in its walls at least one lateral upper outlet opening.

15. An arrangement according to claim 12, wherein the lateral outlet opening is directly below the section of the inherent curvature of the tip of the mandrin.

16. An arrangement according to claim 12, wherein the lateral opening is positioned in a greater distance below the tip of the mandrin and opposite of the drainage opening of the ureter tube.

17. An arrangement according to claim 1, wherein the mandrin or inner mandrin is a flexible metal tube or plastic tube.

18. An arrangement according to claim 1, wherein the mandrin or inner mandrin or outer mandrin has a connecting-piece for the X-ray contrast medium or an attachment for affixing a syringe containing the X-ray contrast medium.

* * * * *